United States Patent
Massoudian et al.

(10) Patent No.: US 12,277,150 B2
(45) Date of Patent: Apr. 15, 2025

(54) COMPUTING TECHNOLOGIES FOR HIERARCHIES OF CHATBOT APPLICATION PROGRAMS OPERATIVE BASED ON DATA STRUCTURES CONTAINING UNSTRUCTURED TEXTS

(71) Applicant: Quantem Healthcare, Inc., Lakewood, CA (US)

(72) Inventors: Bobby Massoudian, Lakewood, CA (US); Freddy Sotelo, Lakewood, CA (US); Tony T. Kalajian, Lakewood, CA (US)

(73) Assignee: Quantem Healthcare, Inc., Lakewood, CA (US)

( * ) Notice: Subject to any disclaimer, the term of this patent is extended or adjusted under 35 U.S.C. 154(b) by 42 days.

(21) Appl. No.: 18/377,635

(22) Filed: Oct. 6, 2023

(65) Prior Publication Data

US 2025/0028743 A1   Jan. 23, 2025

Related U.S. Application Data

(60) Provisional application No. 63/527,970, filed on Jul. 20, 2023.

(51) Int. Cl.
*G06F 16/00* (2019.01)
*G06F 9/54* (2006.01)
*G06F 16/3329* (2025.01)
*G16H 10/60* (2018.01)

(52) U.S. Cl.
CPC .......... *G06F 16/3329* (2019.01); *G06F 9/547* (2013.01); *G16H 10/60* (2018.01)

(58) Field of Classification Search
CPC ............. G06F 16/3331; G06F 16/3334; G06F 16/3335; G06F 16/3338; G06F 16/3329; G06F 9/547; G16H 10/60
USPC ........................................................ 707/767
See application file for complete search history.

(56) References Cited

U.S. PATENT DOCUMENTS

| | | | |
|---|---|---|---|
| 10,498,898 B2 | 12/2019 | Mazza et al. | |
| 10,757,044 B2 | 8/2020 | Fawcett | |
| 11,069,437 B1 * | 7/2021 | Artusy | G16H 80/00 |
| 11,416,682 B2 | 8/2022 | Patel et al. | |
| 11,709,989 B1 | 7/2023 | Mohammed et al. | |
| 2018/0330059 A1 * | 11/2018 | Bates | G16H 10/60 |
| 2018/0365383 A1 * | 12/2018 | Bates | G16H 50/20 |
| 2019/0147111 A1 | 5/2019 | Choi et al. | |
| 2019/0279767 A1 * | 9/2019 | Bates | G16H 40/63 |
| 2020/0073982 A1 * | 3/2020 | Kolluri Venkata Sesha | G06F 11/3082 |
| 2020/0118567 A1 | 4/2020 | Horling et al. | |
| 2020/0372055 A1 * | 11/2020 | Joko | G06F 40/268 |
| 2021/0398624 A1 * | 12/2021 | Baum | G06N 3/08 |
| 2021/0406463 A1 * | 12/2021 | Bhutungru | G06F 40/263 |
| 2022/0070296 A1 * | 3/2022 | Friio | H04M 3/5191 |
| 2022/0076812 A1 * | 3/2022 | Kamangar | A61B 5/01 |
| 2022/0108070 A1 * | 4/2022 | Syeda-Mahmood | G06F 40/205 |

(Continued)

*Primary Examiner* — Monica M Pyo
(74) *Attorney, Agent, or Firm* — Dentons US LLP

(57) ABSTRACT

This disclosure improves computer functionality by enabling various hierarchies of chatbot application programs operative based on data structures containing unstructured texts. Therefore, such hierarchies enable some chatbot application programs to manage other chatbot application programs, which improves virtual assistance, reduces programming efforts, customizes output by user types, and enhances process management.

26 Claims, 4 Drawing Sheets

(56) References Cited

U.S. PATENT DOCUMENTS

| | | |
|---|---|---|
| 2022/0392445 A1 | 12/2022 | Jhaveri |
| 2023/0139397 A1* | 5/2023 | Zhong .................... G06F 40/30 704/9 |
| 2023/0153687 A1 | 5/2023 | Vu et al. |
| 2023/0308405 A1 | 9/2023 | Zabrzenski |

* cited by examiner

COMPUTING TECHNOLOGIES FOR HIERARCHIES OF CHATBOT APPLICATION PROGRAMS OPERATIVE BASED ON DATA STRUCTURES CONTAINING UNSTRUCTURED TEXTS

CROSS-REFERENCE TO RELATED PATENT APPLICATION

This patent application claims a benefit of priority to U.S. Provisional Patent Application 63/527,970 filed 20 Jul. 2023; which is incorporated by reference herein for all purposes.

TECHNICAL FIELD

This disclosure relates to chatbot application programs.

BACKGROUND

Conventionally, a user may operate a computing terminal (e.g., a desktop computer) to chat with a chatbot application program (e.g., ChatGPT). Although this technology may sometimes be useful, this technology still suffers from various technological problems. First, the chatbot application program is not known to be capable of managing other chatbot application programs to enable assistance in chatting with the user operating the computing terminal. Second, the chatbot application program is not known to be capable of managing other chatbot application programs by unstructured text in chatting with the user operating the computing terminal. Third, the chatbot application is not known to be capable of managing other chatbot application programs to customize its output based on user type in chatting with the user operating the computing terminal. Fourth, the chatbot application is not known to be capable of managing other chatbot application programs to follow a process having a set of phases in chatting with the user operating the computing terminal.

SUMMARY

This disclosure at least partially solves at least some technological problems mentioned above. In particular, this disclosure improves computer functionality by enabling various hierarchies of chatbot application programs operative based on data structures containing unstructured texts. Therefore, such hierarchies enable some chatbot application programs to manage other chatbot application programs, which improves virtual assistance, reduces programming efforts, customizes output by user types, and enhances process management, as further described below.

There may be an embodiment including a system, comprising: a cloud computing instance programmed to: access a data structure storing a listing of chatbot application programs recited in unstructured text, a set of configuration parameters recited in unstructured text, a set of prompt templates recited in unstructured text, a set of user types recited in unstructured text, and an outline of a process having a set of phases recited in unstructured text; and host a manager chatbot application program and a set of worker chatbot application programs, wherein the set of configuration parameters enables the manager chatbot application program and the set of worker chatbot application programs to operate pursuant to the set of prompt templates custom to the set of user types based on the listing of chatbot application programs referencing the manager chatbot application program and the set of worker chatbot application programs, such that the manager chatbot application program: receives a prompt originating from a computing terminal external to the cloud computing instance, wherein the prompt requests a task be performed; manages the set of worker chatbot application programs to perform a set of subtasks enabled to collectively perform the task pursuant to the set of phases as guided by the listing of chatbot application programs, the set of configuration parameters, the set of prompt templates, the set of user types, and the outline; generates a reply to the prompt based on the set of subtasks being performed by the set of worker chatbot application programs, thereby collectively performing the task; and sends the reply for consumption on the computing terminal responsive to the prompt.

There may be an embodiment including a method, comprising: operating a cloud computing instance programmed to: access a data structure storing a listing of chatbot application programs recited in unstructured text, a set of configuration parameters recited in unstructured text, a set of prompt templates recited in unstructured text, a set of user types recited in unstructured text, and an outline of a process having a set of phases recited in unstructured text; and host a manager chatbot application program and a set of worker chatbot application programs, wherein the set of configuration parameters enables the manager chatbot application program and the set of worker chatbot application programs to operate pursuant to the set of prompt templates custom to the set of user types based on the listing of chatbot application programs referencing the manager chatbot application program and the set of worker chatbot application programs, such that the manager chatbot application program: receives a prompt originating from a computing terminal external to the cloud computing instance, wherein the prompt requests a task be performed; manages the set of worker chatbot application programs to perform a set of subtasks enabled to collectively perform the task pursuant to the set of phases as guided by the listing of chatbot application programs, the set of configuration parameters, the set of prompt templates, the set of user types, and the outline; generates a reply to the prompt based on the set of subtasks being performed by the set of worker chatbot application programs, thereby collectively performing the task; and sends the reply for consumption on the computing terminal responsive to the prompt.

There may be an embodiment including a storage medium storing a set of instructions executable by a processing unit thereby enabling the processing unit to at least partially perform a method, comprising: operating a cloud computing instance programmed to: access a data structure storing a listing of chatbot application programs recited in unstructured text, a set of configuration parameters recited in unstructured text, a set of prompt templates recited in unstructured text, a set of user types recited in unstructured text, and an outline of a process having a set of phases recited in unstructured text; and host a manager chatbot application program and a set of worker chatbot application programs, wherein the set of configuration parameters enables the manager chatbot application program and the set of worker chatbot application programs to operate pursuant to the set of prompt templates custom to the set of user types based on the listing of chatbot application programs referencing the manager chatbot application program and the set of worker chatbot application programs, such that the manager chatbot application program: receives a prompt originating from a computing terminal external to the cloud computing instance, wherein the prompt requests a task be performed; manages the set of worker chatbot application programs to perform a set of subtasks enabled to collectively perform the task pursuant to the set of phases as guided by the listing of chatbot application programs, the set of configuration parameters, the set of prompt templates, the set of user types, and the outline; generates a reply to the prompt based on the set of subtasks being performed by the set of worker chatbot application programs, thereby collectively performing the task; and sends the reply for consumption on the computing terminal responsive to the prompt

DETAILED DESCRIPTION

Figure 1:
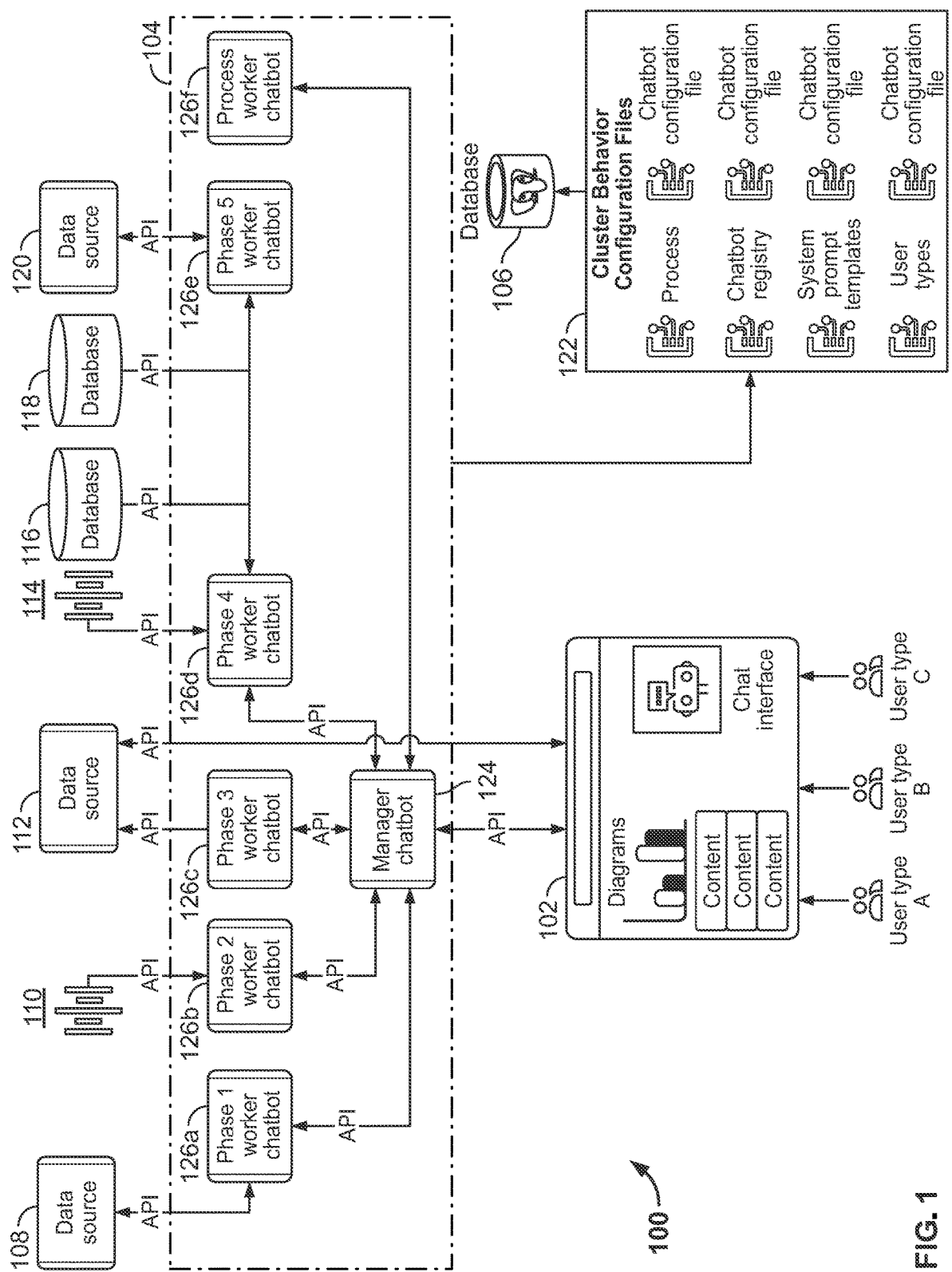
FIG. 1 is a schematic diagram of an embodiment of a system according to this disclosure.

As explained above, this disclosure at least partially solves at least some technological problems mentioned above. In particular, this disclosure improves computer functionality by enabling various hierarchies of chatbot application programs operative based on data structures containing unstructured texts. Therefore, such hierarchies enable some chatbot application programs to manage other chatbot application programs, which improves virtual assistance, reduces programming efforts, customizes output by user types, and enhances process management, as further described below. This disclosure is now described more fully with reference to all attached figures, in which some embodiments of this disclosure are shown. This disclosure may, however, be embodied in many different forms and should not be construed as necessarily being limited to various embodiments disclosed herein. Rather, these embodiments are provided so that this disclosure is thorough and complete, and fully conveys various concepts of this disclosure to skilled artisans. Note that like numbers or similar numbering schemes can refer to like or similar elements throughout.

Various terminology used herein can imply direct or indirect, full or partial, temporary or permanent, action or inaction. For example, when an element is referred to as being "on," "connected" or "coupled" to another element, then the element can be directly on, connected or coupled to the other element or intervening elements can be present, including indirect or direct variants. In contrast, when an element is referred to as being "directly connected" or "directly coupled" to another element, there are no intervening elements present.

As used herein, a term "or" is intended to mean an inclusive "or" rather than an exclusive "or." That is, unless specified otherwise, or clear from context, "X employs A or B" is intended to mean any of natural inclusive permutations. That is, if X employs A; X employs B; or X employs both A and B, then "X employs A or B" is satisfied under any of the foregoing instances. For example, X includes A or B can mean X can include A, X can include B, and X can include A and B, unless specified otherwise or clear from context.

As used herein, each of singular terms "a," "an," and "the" is intended to include a plural form (e.g., two, three, four, five, six, seven, eight, nine, ten, tens, hundreds, thousands, millions) as well, including intermediate whole or decimal forms (e.g., 0.0, 0.00, 0.000), unless context clearly indicates otherwise. Likewise, each of singular terms "a," "an," and "the" shall mean "one or more," even though a phrase "one or more" may also be used herein.

As used herein, each of terms "comprises," "includes," or "comprising," "including" specify a presence of stated features, integers, steps, operations, elements, or components, but do not preclude a presence or addition of one or more other features, integers, steps, operations, elements, components, or groups thereof.

As used herein, when this disclosure states herein that something is "based on" something else, then such statement refers to a basis which may be based on one or more other things as well. In other words, unless expressly indicated otherwise, as used herein "based on" inclusively means "based at least in part on" or "based at least partially on."

As used herein, terms, such as "then," "next," or other similar forms are not intended to limit an order of steps. Rather, these terms are simply used to guide a reader through this disclosure. Although process flow diagrams may describe some operations as a sequential process, many of those operations can be performed in parallel or concurrently. In addition, the order of operations may be re-arranged.

As used herein, a term "response" or "responsive" are intended to include a machine-sourced action or inaction, such as an input (e.g., local, remote), or a user-sourced action or inaction, such as an input (e.g., via user input device).

As used herein, a term "about" or "substantially" refers to a +/−10% variation from a nominal value/term.

Although various terms, such as first, second, third, and so forth can be used herein to describe various elements, components, regions, layers, or sections, note that these elements, components, regions, layers, or sections should not necessarily be limited by such terms. Rather, these terms are used to distinguish one element, component, region, layer, or section from another element, component, region, layer, or section. As such, a first element, component, region, layer, or section discussed below could be termed a second element, component, region, layer, or section, without departing from this disclosure.

Unless otherwise defined, all terms (including technical and scientific terms) used herein have a same meaning as commonly understood by skilled artisans to which this disclosure belongs. These terms, such as those defined in commonly used dictionaries, should be interpreted as having a meaning that is consistent with their meaning in context of relevant art and should not be interpreted in an idealized or overly formal sense, unless expressly so defined herein.

Features or functionality described with respect to certain embodiments may be combined and sub-combined in or with various other embodiments. Also, different aspects, components, or elements of embodiments, as disclosed herein, may be combined and sub-combined in a similar manner as well. Further, some embodiments, whether individually or collectively, may be components of a larger system, wherein other procedures may take precedence over or otherwise modify their application. Additionally, a number of steps may be required before, after, or concurrently with embodiments, as disclosed herein. Note that any or all methods or processes, as disclosed herein, can be at least partially performed via at least one entity or actor in any manner.

Hereby, all issued patents, published patent applications, and non-patent publications that are mentioned or referred to in this disclosure are herein incorporated by reference in their entirety for all purposes, to a same extent as if each individual issued patent, published patent application, or non-patent publication were specifically and individually indicated to be incorporated by reference. To be even more clear, all incorporations by reference specifically include those incorporated publications as if those specific publications are copied and pasted herein, as if originally included in this disclosure for all purposes of this disclosure. Therefore, any reference to something being disclosed herein includes all subject matter incorporated by reference, as explained above. However, if any disclosures are incorporated herein by reference and such disclosures conflict in part or in whole with this disclosure, then to an extent of the conflict or broader disclosure or broader definition of terms, this disclosure controls. If such disclosures conflict in part or in whole with one another, then, to an extent of conflict, the later-dated disclosure controls.

FIG. 1 is a schematic diagram of an embodiment of a system according to this disclosure. In particular, there is a system 100 including a computing terminal 102, a cloud computing instance 104, a database 106, a data source 108, a converter 110, a data source 112, a converter 114, a database 116, a database 118, and a data source 120. The database 106 stores a set of files 122. The cloud computing instance 104 hosts a manager chatbot application program 124 and a set of worker chatbot application programs 126*a-f*. As shown in FIG. 1, the manager chatbot application program 124 is labeled as a manager chatbot, the worker chatbot application program 126*a* is labeled as a Phase 1 worker chatbot, the worker chatbot application program 126*b* is labeled as a Phase 2 worker chatbot, the worker chatbot application program 126*c* is labeled as a Phase 3 worker chatbot, the worker chatbot application program 126*d* is labeled as a Phase 4 worker chatbot, the worker chatbot application program 126*e* is labeled as a Phase 5 worker chatbot, and the worker chatbot application program 126*f* is labeled as a process worker chatbot.

The computing terminal 102 (e.g., a desktop computer, a laptop computer, a tablet computer, a smartphone computer, a wearable computer) communicates with the cloud computing instance 104 via an application programming interface (API) over a network (e.g., a wide area network (WAN), a local area network (LAN)). For example, the API may be a Representational State Transfer (REST) API. The database 106 is deployed external to the cloud computing instance 104, although the database 106 may be deployed internal to the cloud computing instance 104. The database 106 may be a vector database to enable for fast and accurate similarity searches and retrieval of data based on respective vector distances or similarities sourced from the set of files 122, although other suitable data structures (e.g., arrays, vectors, trees, graphs, lists), including databases (e.g., relational, graph, object, columnar), may be used. The database 106 may be omitted and the set of files 122 may be deployed external or internal to the cloud computing instance 104.

The set of files 122 contains a listing of chatbot application programs (e.g., a chatbot registry) recited in an unstructured text (e.g., a natural language or a descriptive text), a set of configuration parameters (e.g., a set of configuration files) recited in an unstructured text (e.g., a natural language or descriptive text), a set of prompt templates (e.g., a set of system prompt templates) recited in an unstructured text (e.g., a natural language or descriptive text), a set of user types (e.g., a set of user profiles with a set of computing privileges that are different from each other) recited in an unstructured text (e.g., a natural language or descriptive text), and an outline of a process having a set of phases (e.g., an object undergoing a sequence of actions or events) recited in an unstructured text (e.g., a natural language or descriptive text). To balance various tradeoffs (e.g., memory, speed, modularity, programming, maintenance), each of the listing of chatbot application programs, the set of configuration parameters, the set of prompt templates, the set of user types, and the outline may be stored in its own data file (e.g., a word processor file, a text file), or at least two of the listing of chatbot application programs, the set of configuration parameters, the set of prompt templates, the set of user types, and the outline may be stored in a single data file (e.g., a word processor file, a text file), any of which may be delimited, grouped, or segmented by respective content, as needed, suitable for processing, as disclosed herein. Likewise, the set of configuration parameters may be distributed in a group of data files, one data file per subset of configuration parameters, which may correspond to a respective chatbot application. However, this configuration may vary and one data file may store multiple subsets of configuration parameters corresponding to multiple respective chatbot application programs, or one data file may store all of the set configuration parameters corresponding to all chatbot application programs, as disclosed herein. Similarly, the set of files 122 may be omitted and there may be a single file (or a suitable data structure) storing the listing of chatbot application programs, the set of configuration parameters, the set of prompt templates, the set of user types, and the outline, which may be delimited, grouped, or segmented by respective content, as needed, suitable for processing, as disclosed herein.

The cloud computing instance 104 may be programmed to access the database 106 (or another suitable data structure) storing the listing of chatbot application programs recited in the unstructured text, the set of configuration parameters recited in the unstructured text, the set of prompt templates recited in the unstructured text, the set of user types recited in the unstructured text, and the outline of the process having the set of phases recited in the unstructured text. As such, the set of configuration parameters enables the manager chatbot application program 124 and the set of worker chatbot application programs 126*a-f* to operate pursuant to the set of prompt templates custom to the set of user types based on the listing of chatbot application programs referencing the manager chatbot application program 124 and the set of worker chatbot application programs 126*a-f*. As explained above, the database 106 may be a data structure, whether a single data file or a set of data files. For example, when the data structure is the set of data files, then the set of data files may contain a first data file storing the listing of chatbot application programs, a second data file storing the set of configuration parameters, a third data file storing the set of prompt templates, a fourth data file storing the set of user types, and a fifth data file storing the outline, although this can vary, as explained above. Likewise, the database 106 may be a vector database, although this form factor can vary, as explained above.

The manager chatbot application program 124 has a one-to-many correspondence with the set of worker chatbot application programs 126*a-f*. However, note that other suitable forms of correspondence are possible (e.g., many-to-many, many-to-one, one-to-one). Although the manager chatbot application program 124 manages the set of worker chatbot application programs 126*a-f* deployed in one logical tier, this configuration is not required. As such, each worker chatbot application program 126*a-f* may itself be a manager chatbot application program and manage other chatbot application programs, similar to a tree nodal network structure or a graph nodal network structure, whether on one logical tier or multiple logical tiers, or the manager chatbot application program 124, which may thereby enable various correspondences (e.g., one-to-one, one-to-many, many-to-many, many-to-one). For example, such configurations may enable sets of sets or clusters of clusters of chatbot applications to manage and submanage tasks and subtasks, as further refined, as needed, as disclosed herein. Note that in such configurations, the listing of chatbot application programs recited in the unstructured text, the set of configuration parameters recited in the unstructured text, the set of prompt templates recited in the unstructured text, the set of user types recited in the unstructured text, and the outline of the process having the set of phases recited in the unstructured text, or other variations on such content may be suitably adapted, as disclosed herein.

The manager chatbot application program 124 may be powered or driven by a large language model (LLM), whether internal thereto or referenced therein, trained (e.g., structured, programmed) to enable the manager chatbot application program 124 to perform its functions, as disclosed herein. For example, the LLM may be a generic model (e.g., an OpenAI's ChatGPT model, a Google Bard model) or a specific-purposes model trained accordingly (e.g., on a purpose-specific terminology).

Each worker chatbot application 126*a-f* may be respectively powered or driven by an LLM, whether internal thereto or referenced therein, trained (e.g., structured, programmed) to enable that respective worker chatbot application 126*a-f* to perform its functions, as disclosed herein. For example, the LLM may be a generic model (e.g., an OpenAI's ChatGPT model, a Google Bard model) or a specific-purposes model trained accordingly (e.g., on a purpose-specific terminology).

The LLM for the manager chatbot application program 124 may be trained differently from at least some, many, most, or all LLMs for the set of worker chatbot application programs 126*a-f*. Likewise, at least some, many, most, or all LLMs for the set of worker chatbot application programs 126*a-f* may be trained differently from each other. However, these configurations are not required. For example, the LLM for the manager chatbot application program 124 may be trained identically to at least some, many, most, or all LLMs for the set of worker chatbot application programs 126*a-f*. Likewise, at least some, many, most, or all LLMs for the set of worker chatbot application programs 126*a-f* may be trained identical to each other.

The manager chatbot application program 124 may be programmed to receive a prompt (e.g., a descriptive user request recited in a natural language) originating from the computing terminal 102 external to the cloud computing instance 104, where the prompt requests a task be performed. For example, the prompt may be submitted to the manager chatbot application program 124 via an API. For example, the API may be a REST API. The manager chatbot application program 124 may decorate (e.g., customize, edit, append, remove, reformat, reorganize) the prompt based on at least one prompt template from the set of prompt templates according to at least one user type of the set of user types. For example, the manager chatbot application program 124 may consider a user type submitting the prompt via a user profile associated with the prompt, select a prompt template, and then decorate the prompt in a manner suitable for the user type. For example, if the user type is A, then the prompt may be decorated in a first manner according to a prompt template A, but if the user type is B, then the prompt may be decorated in a second manner but still according to the prompt template A. Alternatively, if the user type is A, then the prompt may be decorated in a first manner according to a prompt template A, but if the user type is B, then the prompt may be decorated in a second manner according to a prompt template B.

The manager chatbot application program 124 may be programmed to manage the set of worker chatbot application programs 126*a-f* to perform a set of subtasks enabled to collectively perform the task pursuant to the set of phases as guided by the listing of chatbot application programs, the set of configuration parameters, the set of prompt templates, the set of user types, or the outline. The manager chatbot application program 124 may be programmed to manage the set of worker chatbot application programs 126*a-f* to perform the set of subtasks by interfacing with a respective for API for each worker chatbot application program in the set of worker chatbot application programs 126*a-f*. However, this configuration is not required. For example, there may be a single API for the set of worker chatbot application programs 126*a-f*, or there may be some APIs for some worker chatbot application programs 126*a-f* and no APIs for other worker chatbot application programs 126*a-f*, or there may be no APIs at all for managing the set of worker chatbot application programs 126*a-f*, such that the manager chatbot application program 124 manages the set of worker chatbot application programs 126*a-f* in non-API manners (e.g., by messaging, chats, emails).

The master chatbot application program 124 may be programmed to form the set of subtasks pursuant to the set of phases as guided by the listing of chatbot application programs, the set of configuration parameters, the set of prompt templates, the set of user types, or the outline. However, note that this configuration is not required and at least one worker chatbot application program 126*a-f* of the set of worker chatbot application programs 126*a-f* may be programmed to form the set of subtasks pursuant to the set of phases as guided by the listing of chatbot application programs, the set of configuration parameters, the set of prompt templates, the set of user types, or the outline, as managed by the manager chatbot application program 124.

The set of subtasks may correspond to the set of phases, which may be a one-to-one correspondence, although other suitable forms of correspondence (e.g., one-to-many, many-to-one, many-to-many) are possible. For example, if the outline describes the process to have five phases, then the set of subtasks may have five subtasks, which may total to worker chatbot application programs 126*a-f*, or one less if one chatbot application program 126*a-f* forms the set of subtasks. Each worker chatbot application program 126*a-f* of the set of worker chatbot application programs 126*a-f* may be programmed to be dedicated to performance of a single respective subtask of the set of subtasks, although at least some worker chatbot application programs 126*a-f* may be programmed to perform at least two subtasks of the set of subtasks. The set of subtasks may include a first subtask and a second subtask.

The set of worker chatbot application programs 126*a-f* may contain a first worker chatbot application program 126*a-f* and a second worker chatbot application program 126*a-f*, where the first worker chatbot application program 126*a-f* may be programmed to prompt the second worker chatbot application program 126*a-f* (or the manager chatbot application program 124). For example, the first worker chatbot application program 126*f* may form the set of subtasks and then prompt the second chatbot application program 126*d* or 126*e* to perform at least one subtasks of the set of subtasks (or the manager chatbot application program 124). Likewise, the first worker chatbot application program 126*d* may perform at least one subtask of the set of subtasks and then prompt the second worker chatbot application program 126*e* based on that respective subtask being completed, which may be needed for informational sharing (e.g., a set of data for one subtask may be needed for another subtask), dependency of performance (e.g., a competition of one subtask may be needed for performance of another subtask), or cascading of at least some subtasks on other subtasks (e.g., a success or completion of one subtask leads to a beginning of performance of another subtask). Similarly, the first subtask may involve an object detection algorithm (locally or remotely performed), an edge detection algorithm (locally or remotely performed), or another suitable computer vision algorithm performed (locally or remotely) on a medical image (e.g., an X-ray image, a magnetic resonance image (MRI)), such that a content is generated to enable the second subtask to be performed. Note that at least two subtasks of the set of subtasks may be performed in sequence, out of sequence, simultaneously, or in parallel.

The manager chatbot application program 124 may be programmed to generate a reply to the prompt based on the set of subtasks being performed by the set of worker chatbot application programs 126*a-f*, thereby collectively performing the task. The manager chatbot application program 124 may be programmed to send the reply for consumption (e.g., via a display or a speaker), on the computing terminal 102 responsive to the prompt. For example, the reply may be sent to the computing terminal 102 via an API. For example, the API may be a REST API.

Although the set of worker chatbot application programs 126*a-f* contains six worker chatbot application programs, this configuration is not required. As such, there could be less or more than six (e.g., one, two, three, four, five, seven, eight, nine, ten, tens, dozens, hundreds, thousands), as needed, as disclosed herein. For example, more complicated tasks and subtasks could have this amount to be higher than six (e.g., seven, eight, nine, ten, tens, dozens, hundreds, thousands), whereas less complicated tasks and subtasks could have this amount to be less than six (e.g., one, two, three, four, five), where each task and subtask may be further subtasked as needed, as disclosed herein.

In order to perform the set of subtasks, at least some worker chatbot application programs of the set of worker chatbot application programs 126*a-f* may need to interact (e.g., communicate, engage, prompt, query, ping) with other (e.g., third party) computing entities (e.g., servers, APIs, databases) deployed external to the cloud computing instance 104. The other computing entities may include the data source 108, the converter 110, the data source 112, the converter 114, the database 116, the database 118, or the data source 120. Although the data source 108, the converter 110, the data source 112, the converter 114, the database 116, the database 118, or the data source 120 are separate and distinct from each other, this configuration is not required. For example, at least two of the data source 108, the converter 110, the data source 112, the converter 114, the database 116, the database 118, or the data source 120 be joined or operate as a single computing entity. For example, the converter 110 and the convert 114 are separate and distinct from each other, but can be a single converter. Likewise, the data source 108, the data source 112, and the data source 120 are separate and distinct from each other, but at least two of the data source 108, the data source 112, or the data source 120 can be a single data source. Similarly, the database 116 and the database 118 are separate and distinct from each other, but can be a single database.

At least one worker chatbot application program of the set of worker chatbot application programs 126*a-f* may be programmed to access (e.g., over a network, a WAN, a LAN) an API deployed external to the cloud computing instance 104, such that the API outputs a set of information (e.g., a text string, a data file, an image, a sound, a word processor file, a spreadsheet file, a text file, a configuration file) to that worker chatbot application program. For example, the API can be a REST API. The set of information may enable that worker chatbot application program to perform at least one subtask of the set of subtasks using (e.g., reading, editing, extracting, construing) or based on the set of information, whether solely or together with other information accessible to the cloud computing instance 104, whether internal or external to the cloud computing instance (e.g., the set of files 122, the manager chatbot application 124, the set of worker chatbot application programs 126*a-f*). The API may interact (e.g., communicate, engage, prompt, query, ping) with the data source 108, the converter 110, the data source 112, the converter 114, the database 116, the database 118, or the data source 120 as needed to retrieve the set of information, whether the API is deployed internal or external to the data source 108, the converter 110, the data source 112, the converter 114, the database 116, the database 118, or the data source 120.

At least one worker chatbot application program of the set of worker chatbot application programs 126*a-f* may be programmed to access the API based on inputting a user identifier (e.g., a personal identification number (PIN), a login) to the API, such that the set of information output by the API is specific to the user identifier and at least one subtask of the set of subtasks is specific to the user identifier. For example, the data source 108 may use the user identifier to source the set of information to the API.

At least one worker chatbot application program of the set of worker chatbot application programs 126*a-f* may be programmed to access the API to request a conversion (e.g., automatic) of a content from a first data format (e.g., audio, image, text) into a second data format (e.g., text, audio, text), whether at the API or the data source 108, the converter 110, the data source 112, the converter 114, the database 116, the database 118, or the data source 120. As, such, the API may receive the content in the first data format from at least one worker chatbot application program of the set of worker chatbot application programs 126*a-f*, convert or request conversion of the content from the first data format to the second data format, and output the content in the second format to that worker chatbot application program. For example, the converter 110 or the converter 114 may convert the content from the first data format to the second data format. For example, the set of information may be a speech-to-text transcription (e.g., a data file, a web page, a word processing document) formed from a recording of an audio content (or containing the audio content) provided to the API. In this case, the prompt originating from the computing terminal 102 may include or reference the recording, or the recording may be sourced from the data source 108, the converter 110, the data source 112, the converter 114, the database 116, the database 118, or the data source 120. For example, when the prompt originating from the computing terminal 102 include or reference the recording, the manager chatbot application program 124 may share the recording with that worker chatbot application program accessing the API to convert or request conversion of the recorder. If the set of information is the speech-to-text transcription, then that worker chatbot application program (or another worker chatbot application program or the manager chatbot application program 124) may be programmed to form a summary (e.g., via an automatic summarization algorithm, an extraction-based summarization algorithm, an abstractive-based summarization) of the speech-to-text transcription, to enable the manager chatbot application program 124 to take an action based on the summary. The action can be of various types. For example, the action can be prompting another worker chatbot application program of the set of worker chatbot application programs 126a-f to do something (e.g., issue a notice, prompt another worker chatbot application program, engage an API, query a database). For example, the action can be prompting the manager chatbot application program 124 to do something (e.g., issue a notice, prompt another worker chatbot application program, engage an API, query a database).

The cloud computing instance 104 may host a database (e.g., a relational database, a NoSQL database, a vector database, an object database, a graph database) storing a record containing a set of information (e.g., a set of fields storing a set of attributes) for a user identifier (e.g., a PIN, a login). As such, at least one worker chatbot application program of the set of worker chatbot application programs 126a-f may be programmed to perform at least one subtask of the set of subtasks relating to the user identifier by retrieving (e.g., reading, copying) the set of information from the record, forming a summary (e.g., via an automatic summarization algorithm, an extraction-based summarization algorithm, an abstractive-based summarization) of the set of information, and sending the summary to the manager chatbot application program 124 to enable the manager chatbot application program 124 to take an action based on the summary. The action can be of various types. For example, the action can be prompting another worker chatbot application program to perform another subtask relating to the user identifier. For example, the action can be prompting another worker chatbot application program of the set of worker chatbot application programs 126a-f to do something (e.g., issue a notice, prompt another worker chatbot application program, engage an API, query a database).

At least one worker chatbot application program of the set of worker chatbot application programs 126a-f may be programmed to access a first API (e.g., a REST API) external to the cloud computing instance 104, such that the first API outputs a first set of information (e.g., a text string, a data file, an image, a sound, a word processor file, a spreadsheet file, a text file, a configuration file) to that worker chatbot application program, to enable that worker chatbot application program to perform at least one subtask of the set of subtasks. The computing terminal 102 may be programmed to access a second API (e.g., a REST API) external to the cloud computing instance 104, such that the second API outputs a second set of information (e.g., a text string, a data file, an image, a sound, a word processor file, a spreadsheet file, a text file, a configuration file) for consumption (e.g., via a display or a speaker) on the computing terminal 102. The first API may be logically positioned (e.g., deployed) between that worker chatbot application program and a data source and the second API may be logically positioned (e.g., deployed) between the computing terminal 120 and the data source. For example, the data source may be the data source 112. For example, the cloud computing instance 104 may be logically positioned (e.g., deployed) between the computing terminal 102 and the second API. For example, the cloud computing instance 104 may not be logically positioned (e.g., deployed) between the computing terminal 102 and the second API. For example, the first API and the second API may be separate and distinct from each other, or may be one API. For example, the first set of information and the second set of information may be separate and distinct from each other, or may be one set of information. For example, the first set of information or the second set of information may relate to a user identifier (e.g., a PIN, a login), where the data source sources the first set of information or the second set of information based on that worker chatbot application program or the computing terminal 102 providing the first API or the second API with the user identifier. For example, the first set of information and the second set of information may be sourced from or be an electronic health record (EHR) associated with the user identifier.

At least two worker chatbot application programs of the set of worker chatbot application programs 126a-f may be each programmed to access a first database (e.g., a relational database, a NoSQL database, a vector database, an object database, a graph database) and a second database (e.g., a relational database, a NoSQL database, a vector database, an object database, a graph database). For example, the first database may be the database 116 and the second database may be the database 118. The first database may be accessed via a first API (e.g., a REST API) and the second database may be accessed via a second API (e.g., a REST API). The first API and the second API may be separate and distinct APIs or one API. The first database may source a first set of codes classified according to a first classification and the second database may source a second set of codes classified according to a second classification. The first set of codes or the second set of codes may be used by any of these two worker chatbot application programs to perform a respective subtask.

Although the set of worker chatbot application programs 126a-f may need to interact with other computing entities deployed external to the cloud computing instance 104 via the API, this configuration is not required. As such, the set of worker chatbot application programs 126a-f may need to interact with other computing entities deployed external to the cloud computing instance 104 directly or in other ways that do not involve the API. For example, the API may be omitted.

Figure 2:
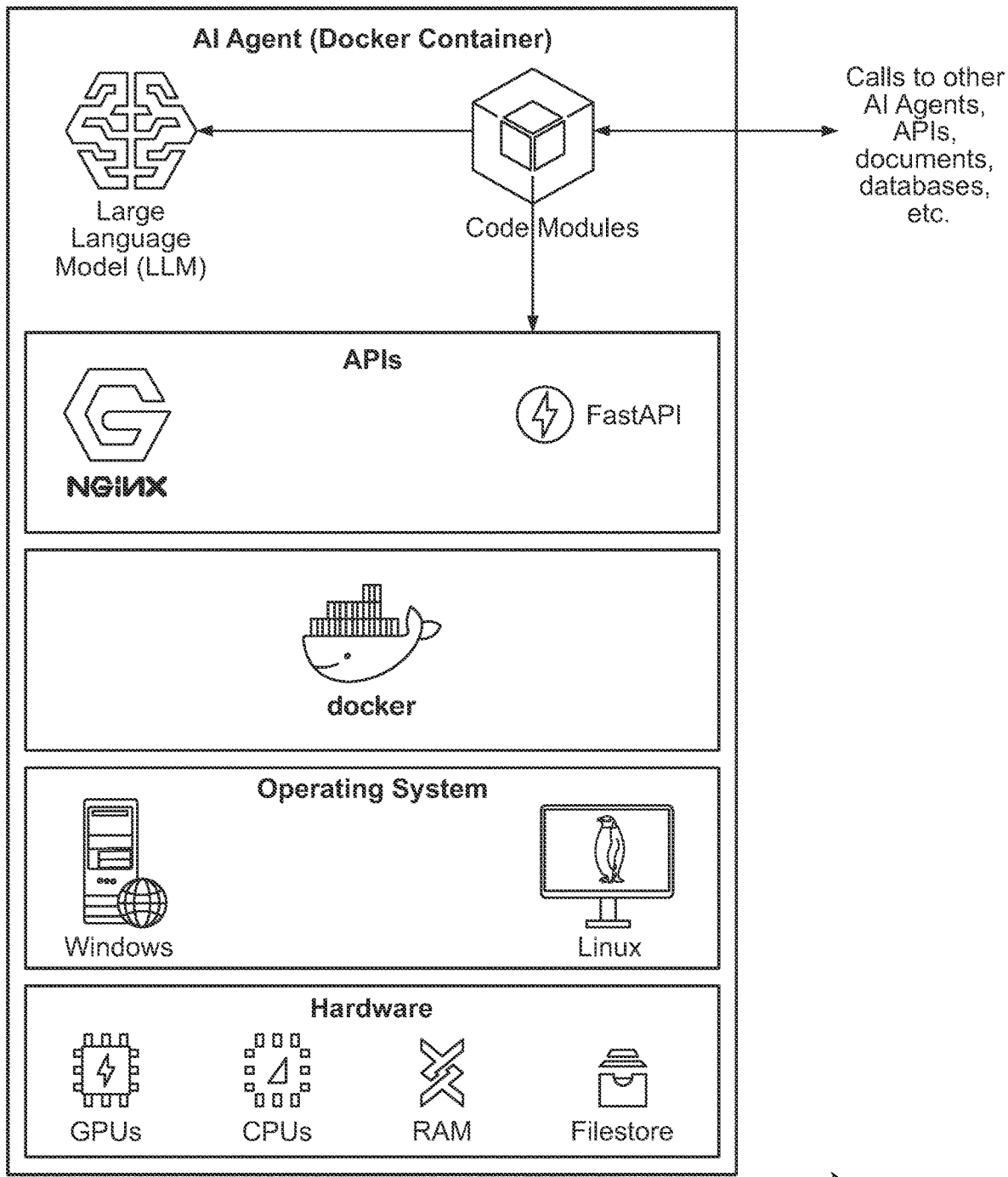
FIG. 2 is a schematic diagram of an embodiment of a chatbot application program according to this disclosure.

FIG. 2 is a schematic diagram of an embodiment of a chatbot application program according to this disclosure. In particular, there is a schematic diagram 200 of a chatbot application program, whether master or worker, that is programmed to operate, as disclosed in context of FIG. 1. Note that this layer model is not required and the chatbot application may be configured differently.

Figure 3A:
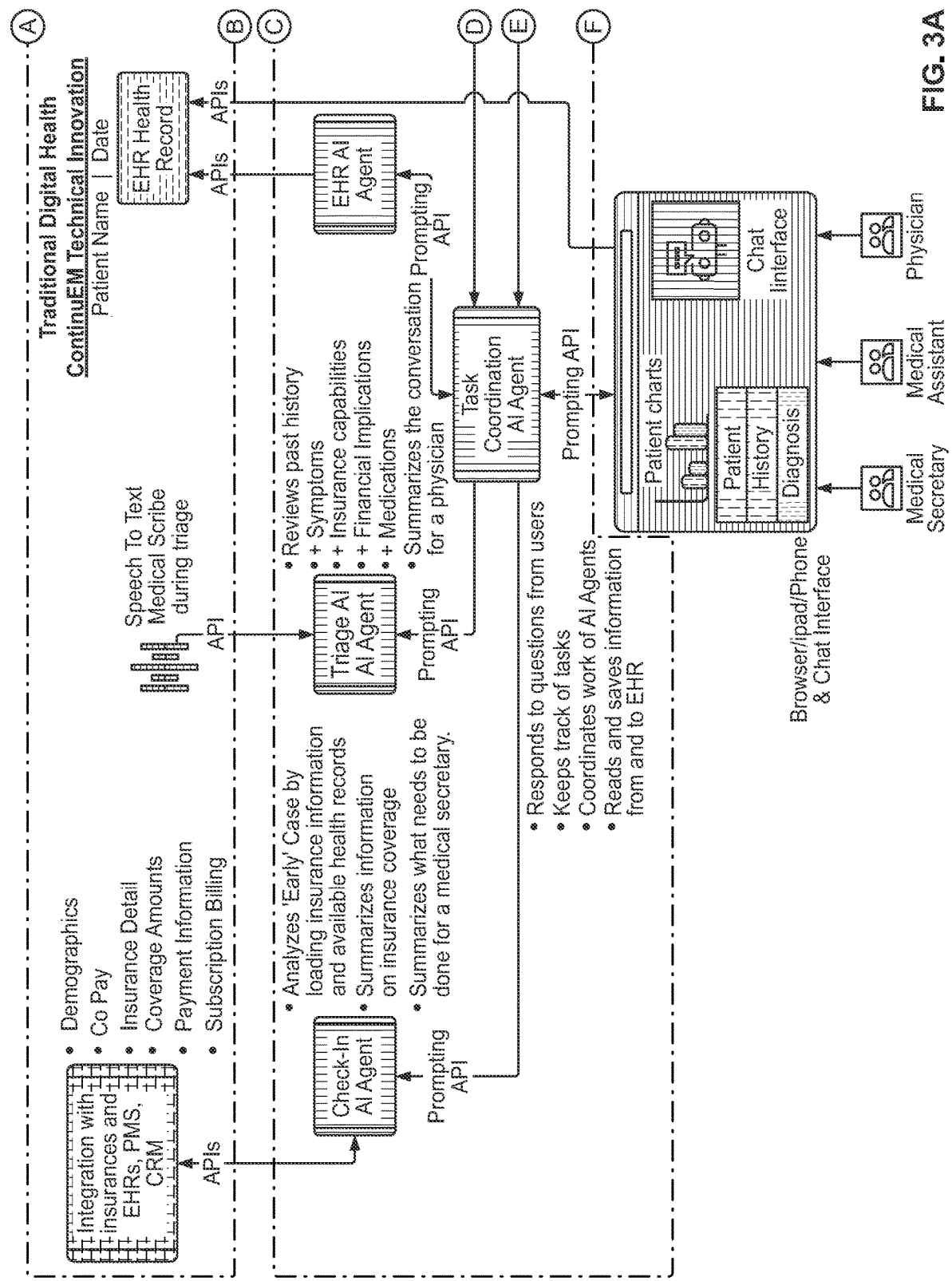
FIGS. 3A and 3B collectively are a schematic diagram of an embodiment of a system according to this disclosure.
Figure 3B:
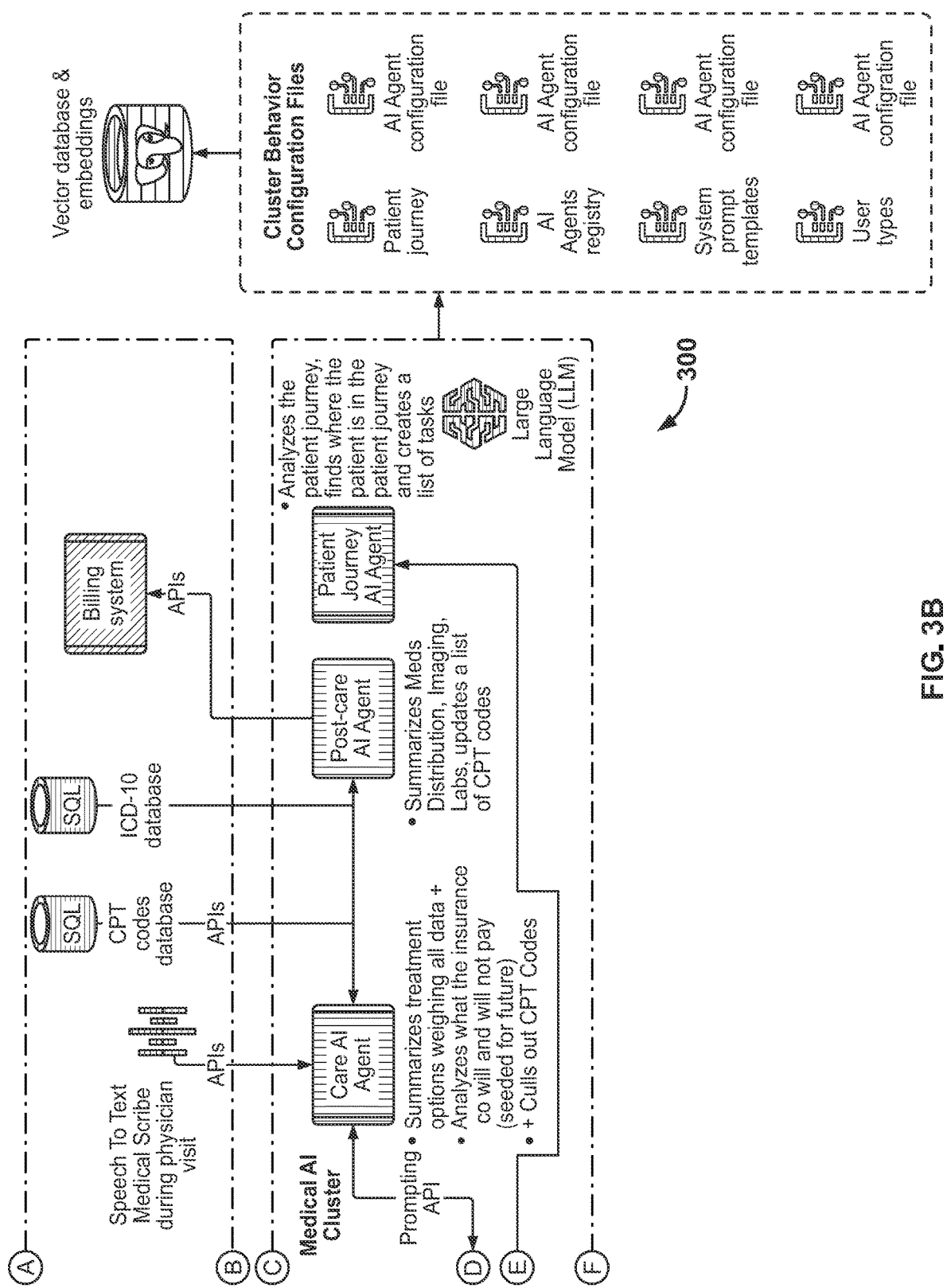

FIGS. 3A and 3B are collectively a schematic diagram of an embodiment of a system according to this disclosure. In particular, a system 300 is an embodiment of the system 100, as applied to digital healthcare. However, note that such application is not required and the system 100 may be applied to other fields of use (e.g., engineering, law, accounting, finance, law enforcement, military).

The system 300 may enable an intelligent urgent care software system. In particular, there may be a cluster of autonomous artificial intelligence (AI) software agents (e.g., a hierarchy of chatbot application programs 126a-f) logically positioned (e.g., deployed) in-between medical professional users (e.g., a set of computing terminals 102 operated by physicians, nurses, medical assistants, medical secretaries) and a variety of digital health data systems (e.g., a set of electronic health record (HER) systems, medical insurance integration systems, medical billing systems) aimed to simplify and unify a user interface, lower required interactions with different computer systems used in urgent care facilities, automate mundane functions and improve at least some efficiency and speed of patient intake, triage, and care, while also improving virtual assistance, reduces programming efforts, customizes output by user types, and enhances process management, as described above.

Conventionally, certain medical professionals spend more time interacting with computer systems than spending time with patients. For example, a typical measure for a physician is to spend two hours entering data into a variety of computer systems for each hour spent with a patient. Further, certain medical professionals need to spend a lot of time learning how to use different computer systems and interfaces to do their job. As such, the system 300 acts like an intermediary between medical professional users and a variety of computer systems and interfaces used in urgent care facilities (or other medical facilities) taking over a job of gathering and analyzing some, many, most, or all available relevant information needed to provide patient intake, triage, and care, visually presenting that information and summaries to medical professionals users in a chatbot interface. When allowed and possible, the system 300 may interface with various APIs of certain digital health data systems to save medical data approved by medical personnel users into various backend computer systems enabling the system 300 and thus replace or minimize at least some, much, most or all of manual work (e.g., administrative) typically done by medical professionals.

The system 300 may provide a user interface that is internet browser-based (e.g., Firefox, Safari, Edge Chrome), rendered on desktop computers, tablet computers, mobile phones or other computing terminals which may be used by urgent care staff, although dedicated app-versions are possible. Medical professional users may communicate with the system 300 in a chat manner. For example, a medical professional user may ask questions in natural language (e.g., a descriptive text or an unstructured text) and receive information on a variety of topics related to a patient's health, status of all patients, queues, wait periods, or other relevant factoids, as disclosed herein. Therefore, as the patient proceeds through a patient journey with a set of phases (e.g., intake, triage, labs, diagnosis, treatment, procedures, therapy), the system 300 requests, collects, analyzes and processes a variety of data from the digital health data systems and then informs and assists the medical professional users in each phase in the patient journey.

The system 300 may include a first logical unit (a group of chatbot applications), a second logical unit (a group of configuration data sources), a third logical unit (a group of health data sources), and a fourth logical unit (an end user access point). The first logical unit contains a hierarchy of chatbot application programs having the manager chatbot application program 124 and the set of worker chatbot application programs 126a-f, where the manager chatbot application program 124 has a one-to-many correspondence with the set of worker chatbot application programs 126a-f to operate, as disclosed herein. The second logical unit contains a group of configuration data sources (the set of data files 122) containing various configuration data recited in the unstructured text based on which the hierarchy of chatbot application programs is operative, as disclosed herein. The third logical unit contains a group of health data sources (the data source 108, the converter 110, the data source 112, the converter 114, the database 116, the database 118, or the data source 120) sourcing data for the hierarchy of chatbot application programs, as disclosed herein. The fourth logical unit contains the computing terminal 102 (e.g., a desktop computer, a laptop computer, a tablet computer, a smartphone, a wearable computer, a robotic computer, a telepresence robot) operative by an end user (e.g., a medical professional) running an operating system (OS) and an application program (e.g., a web browser application program) running on the OS, where the application program has a viewport presenting a user input field or a set of user input fields through which the user chats with the manager chatbot application program 124 and the manager chatbot application program 124 outputs a content (e.g., a text, an unstructured text, a structured text, an image, a video, a sound) to the user, as disclosed herein.

The hierarchy of chatbot application programs may have each of its chatbot application programs operate based on (1) LLMs that have been appropriately pre-trained, as disclosed herein, and (2) a set of data files, each reciting an unstructured text (e.g., a natural language text, a descriptive text), describing a set of rules the hierarchy of chatbot application programs needs to follow, as disclosed herein. For example, one of such data files may include a file describing an object (e.g., a physical object, a virtual object, an animate object, an inanimate object, a person, an animal, a pet, a patient, a vehicle) going through a set of phases (e.g., intake, triage, labs, diagnosis, treatment, procedures, therapy) in an unstructured text. For example, as a manager of an urgent care facility (or another medical facility), a user may operate a word processing application program (e.g., a Microsoft Word processing application program) running on an OS of a computing terminal to describe how a patient is moving through a patient journey (the object going through the set of phases) in English (or another human language) and have that description saved in a data file, such that the hierarchy of chatbot application programs would interpret the data as the hierarchy of chatbot application programs performs its function, as disclosed herein. Likewise, the set of data files may have a data file reciting an unstructured text describing or providing a list of all relevant integrations to other medical systems (the third logical unit). Similarly, the set of data files may have a data file reciting an unstructured text describing or providing a registry of the hierarchy of chatbot application programs.

The hierarchy of chatbot application programs has the manager chatbot application program 124 and the set of worker chatbot application programs 126a-f operative based on the set of data files 122, such that the set of data files 122 guides the hierarchy of chatbot application programs by description as to how the hierarchy of chatbot application programs having the manager chatbot application program 124 and the set of worker chatbot application programs 126a-f should operate or behave, as disclosed herein. The set of data files 122 may be a repository of documents (e.g., a collection of word processor documents) driving how the hierarchy of chatbot application programs behaves. The hierarchy of chatbot application programs access the set of data files 122, such that the hierarchy of chatbot application programs reads whatever contents are disclosed, construes such contents, analyzes such contents, and use such contents to generate chatbot prompts, invisible to end users, in responses to prompts to get data on what correct behaviors should be.

The set of data files 122 a first data file (e.g., a word processor document, a text file), a second data file (e.g., a word processor document, a text file), a third data file (e.g., a word processor document, a text file), a fourth data file (e.g., a word processor document, a text file), and a fifth data file (e.g., a word processor document, a text file). The first data files contains an unstructured text (e.g., a natural language text, a descriptive text) describing or listing the hierarchy of chatbot application programs, including a respective use and a respective capability for each of such chatbot application programs. The second data file contains an unstructured text (e.g., a natural language text, a descriptive text) describing or listing all respective dependencies (e.g., data files, APIs) that may be needed for a respective chatbot application to function. The third data file contains an unstructured text (e.g., a natural language text, a descriptive text) describing or listing a set of prompt templates used for each respective chatbot application to drive its behavior, where each chatbot application may have a prompt template. The fourth data file contains an unstructured text (e.g., a natural language text, a descriptive text) describing or listing a set of end user types providing and a set of respectively corresponding roles (e.g., a user profile A is a doctor who permissioned to do X). The fifth data file contains an unstructured text (e.g., a natural language text, a descriptive text) describing or listing a process having a set of phases that are consecutive, where the process involves an object going through the set of phases. For example, the object may be a patient and the set of phases may be intake, triage, labs, diagnosis, treatment, procedures, therapy or others. As such, the process may be akin to a patient journey describing how the patient is expected to engage with a medical professional user and how the patient is expect to move through the set of phases in the process.

Each chatbot application program in the hierarchy of chatbot application programs may include, reference, or be operative based on various forms of executable logic (e.g., an application program, a software module, an API, a pre-trained model), as disclosed herein. For example, such executable logic may contain, reference or be operative based on a generative pre-trained transformer (GPT) model, where there can be a general-purpose model (e.g., an OpenAI's ChatGPT model, a Google Bard model) or a specific-purposes model trained accordingly (e.g., on a relevant medical terminology). For example, such executable logic may contain, reference or be operative based on software modules and functions at least some of which may provide an API endpoint to a respective chatbot application program in the hierarchy of chatbot application programs to receive a prompt. For example, such executable logic may contain, reference or be operative based on software modules and functions to call other chatbot application programs in the hierarchy of chatbot application programs. For example, such executable logic may contain, reference or be operative based on software modules and functions to access the set of data files 122 according to which the hierarchy of chatbot application operates or behaves. For example, such executable logic may contain, reference or be operative based on software modules and functions to access integration points and load data therefrom. Some examples of such points include web scrapers, third party APIs, medical scribes, databases, embeddings in vector databases, or others. For example, such executable logic may contain, reference or be operative based on software modules and functions to do self-iterative prompting by using multiple prompting optimization techniques. For example, such executable logic may contain, reference or be operative based on long and short term memory used to keep track of prompts, tasks, and other functions (e.g., a random access memory (RAM), a local permanent storage, a file system). For example, such executable logic may contain, reference or be operative based on real or virtualized hardware and software to run on and execute tasks (e.g., a docker container, a hypervisor, a virtual machine).

The manager chatbot application program 124 may be programmed to interact with the application program running on the OS running on the computing terminal 102 operated by the end user. As such, the manager chatbot application 124 may receive a user request (e.g., a prompt) for performance of a task, segment the request into a set of subtasks collectively performing the task, identify one or more appropriate worker chatbot application programs 126a-f for performing the set of subtasks, prompt those chatbot application programs 126a-f to perform respective subtasks (serially or parallel), analyze answers received from those chatbot application programs 126a-f, formulate an answer to the user request, generate a reply to the user request based on the answer or including the answer, and send the reply to the computing terminal 102 responsive to the user request. The manager chatbot application program 124 and its associated software, whether internal or external, can perform this function because the manager chatbot application program 124 has access to the set of data files 122 (e.g., a patient journey) to know or guide who does what where why and how in context of the set of phases in the process, so that the manager chatbot application program 124 can make a decision which worker chatbot application 126a-f to use, when, and how, as disclosed herein.

For example, below is a pseudocode for a user prompt to perform a task, as disclosed herein, where comments are preceded by // or encased between /* and */.

```
The main frontend application:
    A user logs into a system 300 by using a main frontend application
    If login is valid
        The system loads a user profile
    Else
        Show login error and ask the user for credentials again
    The user inputs a prompt into a chat interface thereby operating as a first
    command
    Decorate user's prompt
    Convert user's prompt into JSON format (or XML or CSV or another suitable
    format that uses human-readable text to store and transmit data objects
    consisting of attribute-value pairs and arrays (or other serializable values))
    Make an API call to a Task Coordination AI Agent (TCA) and pass the JSON
    data to the TCA
In response to an API call, the TCA performs these actions:
    Code Module:
        Load system prompt template into memory
        Load an AI Agents Registry document into memory and append this
        document to the system prompt template
```

```
        Load a Patient Journey document into memory and append this document
        to the system prompt template
        Load a User's Profiles document into memory and append this document
        to the system prompt template
        Set a system prompt for the LLM //This is to prime the AI model so that
        the AI model knows its context
        Set a user prompt for the LLM
        Call the LLM API to generate a response
    LLM:
        In the response to the API call, LLM returns a list of tasks to the code
        module //Each task has an indicator which downstream AI Agent should
        be used
    Code Module:
        Split the response into an array of strings //Each string array element is
        one task
        For each task in the array of tasks
            Extract AI Agent name from the task //e.g., CHECK_IN_AGENT
            Extract the task //e.g. Load insurance information for ...
            Make an API call to the AI Agent with task equal to the prompt //see
            below
            Save the response from the AI Agent into an array of responses
        EndFor
        Concatenate the responses and append an instruction to LLM to
        summarize information
        Set a user prompt for the LLM to the concatenated string from above
        Call the LLM API to generate a summary
        Return a summary to the main frontend application
In the response to the TCA's API call, the AI Agent (e.g., the manager chatbot
application program 124) performs these actions:
    Code Module:
        Load system prompt template into memory
        Load an AI Agent configuration document into memory
        Concatenate the system prompt template and the AI Agent configuration
        files
        Set a system prompt for the LLM //This is to prime the AI model so it
        knows its context and what it can do, which tools (APIs) it is using
        Set a user prompt for the LLM to the task given by TCA
        Call the LLM API to generate a response
    LLM:
        In the response to the API call, LLM returns a list of subtasks to the code
        module //Each sub-task has an indicator which tool (API) should be used
    Code Module:
        Split the response into an array of strings //Each string array element is
        one subtask
        For each subtask in the array of subtasks
            Extract tool name from the subtask //e.g. WEB_SCRAPE_API
            Extract the subtask //e.g. https://something.com/apis?card=...
            Execute an API call with parameters
            Convert JSON to text
            Save the text in an array of responses
        EndFor
        Concatenate the responses and append an instruction to LLM to
        summarize information
        Set a user prompt for the LLM to the concatenated string from above
        Call the LLM API to generate a summary
        Return a summary to TCA
```

For example, below is a pseudocode for a user prompt by a medical secretary originating at a place of care to perform a check-in of a patient who arrived at the place of care (e.g., an urgent care clinic), as disclosed herein, where comments are preceded by // or encased between /* and */.

```
/* A patient arrives at the doctor's office and asks for medical help. The doctor's office
has computing terminals 102 (e.g. desktop computers, laptops, tablets or phones with a
browser based user interface to access AI Based Medical System via a chat interface. */
The main frontend application:
    A medical secretary logs into the system 300 by using the main frontend
    application
    If login is valid
        The system loads user's profile
    Else
        Show login error and ask the user for credentials again
    User inputs a prompt into the chat interface thereby operating as a first command
    /* Example Prompt: "I have a new patient with a medical card from Blue Cross
    Blue Shield (BCBS) with a number 99999999. Patient complains of abdominal
```

-continued pain, tension and heat in his shoulders, feeling of diarrhea but unable to go.
Process the patient information and advise me on the next steps, please." */
Decorate user's prompt
/* An example decorated prompt: "A medical secretary asked the following
question: I have a new patient with a medical card from Blue Cross Blue Shield
of Massachusetts with a number 99999999. Patient complains of abdominal pain,
tension and heat in his shoulders, feeling of diarrhea but unable to go. Process
the patient information and advise me on the next steps, please. Create a list of
tasks with their completion status." */
Convert user's prompt to JSON format (or XML or CSV or another suitable
format that uses human-readable text to store and transmit data objects
consisting of attribute-value pairs and arrays (or other serializable values))
Make an API call to the TCA and pass the JSON data to the TCA
In response to the API call the TCA does the following:
    Code Module:
        Load system prompt template into memory
        /* System prompt: You are a helpful AI agent working for an urgent care
        facility in conjunction with medical staff which relies on a number of
        downstream AI Agents which will execute tasks for you. Your main goal is
        to accept medical staff requests, examine which downstream agents can
        fulfill requests, split the request into tasks and assign them to the
        downstream agents to execute. You have to use this format when
        returning responses:
        [Downstream AI Agent Name 1] Task for the Downstream AI Agent 1.
        [Downstream AI Agent Name 2] Task for the Downstream AI Agent 2.
        [Downstream AI Agent Name 3] Task for the Downstream AI Agent 3.
        ...
        You will find a list of all downstream AI agents below.
        When creating tasks, you will need to consult the section below named
        "Patient Journey". That section has details of how the patient goes through
        the process at the urgent facility. Consult this section when ordering tasks
        because some tasks are dependent on the others being finished first.
        You can find a list of all users in the sections named "Users Profiles"
        below.
        */
        Load an AI Agents Registry document into memory and append it to the
        system prompt template
        /* Example of an AI Agents Registry:
        Available Downstream AI Agents (e.g., worker chatbot application
        programs 126a-f)
        CHECK_IN_AGENT
        This downstream agent is capable of loading insurance information,
        analyzing early patient cases by loading insurance information and
        available health records, summarizing information on insurance coverage,
        and summarizing what needs to be done for a medical secretary.
        Agent's API Endpoint: https://agent1/api
        TRIAGE_AGENT
        This downstream agent is capable of reviewing patient past history,
        symptoms, insurance coverage, financial implications, medications, and
        summarizing the conversation for a physician.
        Agent's API Endpoint: https://agent2/api
        ...
        */
        Load a Patient Journey document into memory and append it to the
        system prompt template
        /* Example of a Patient Journey document:
        Patient Journey
        This document describes processes at an urgent center named
        ContinuEM located at 6430 South St, Lakewood, CA 90713. The urgent
        center has 8 doctors, 20 nurses, and 4 medical secretaries.
        The patient moves through a process defined here. Patients can check in
        to the urgent care online, at the kiosk located in the facility, or by talking to
        a medical secretary at the front desk. Check in is ....
        */
        Load a "User types" document into memory and append it to the system
        prompt template
        /* Example of a Users types document:
        Users Types
        Medical Secretary
        This user is ...
        Medical Assistant
        This user is ...
        Triage Nurse
        This user ...
        */
        Set a system prompt for the LLM //This is to prime the AI model so it
        knows its context. The system prompt is now a combination of a system
        prompt template, downstream agents registry, patient journey, and users
        profiles.

```
        Set a user prompt for the LLM
        Call the LLM API to generate a response
LLM:
        In the response to the API call, LLM returns a list of tasks to the code
        module //Each task has an indicator which downstream AI Agent should
        be used. [PATIENT_JOURNEY_AGENT] Find out which stage of the
        patient journey we are in now.
        [CHECK_IN_AGENT] Load insurance information and save it into the
        EHR for this patient: Blue Cross Blue Shield of Massachusetts card
        number 9999999.
        [TRIAGE_AGENT]: Check the patient's symptoms and alert the medical
        secretary if the symptoms are severe enough to warrant urgent care by a
        physician. These are the symptoms: "abdominal pain, tension and heat in
        his shoulders, feeling of diarrhea but unable to go".
Code Module:
        Split the response into an array of strings //Each string array element is
        one task
        For each task in the array of tasks
                Extract AI Agent name from the task //e.g.
                PATIENT_JOURNEY_AGENT
                Extract the task //e.g. Find out which stage of the patient journey
                we are in now.
                Make an API call to the downstream AI Agent with task equal to the
                prompt
                Save the response from the AI Agent into an array of responses
        EndFor
        Concatenate the responses and append an instruction to LLM to
        summarize information
        Set a user prompt for the LLM to the concatenated string from above
        Call the LLM API to generate a summary
        Return a summary to the main frontend application
        /* The patient is now checked in. Patient name is Chad Gipiti, born
        7/28/1969, middle aged Latino male, has private insurance through his
        employer with a co-pay of $50 per urgent care visit. His out of pocket max
        is $2,000/year. Please bill Chad $50 co-pay for the visit. His PCP is Lexi
        Polivogy at Mass General Hospital in Boston, NPN: 8888. Patient's
        demographics, insurance, and charts are downloaded to the EHR. Chad is
        fully checked in and is ready for the next step in the patient journey which
        is triage. The patient is experiencing symptoms that are often associated
        with heart attack. Please alert a physician to check the patient
        immediately! */
In the response to the TCA's API call, the downstream AI Agent does the following:
Code Module:
        Load system prompt template into memory
        /* Example: You are a helpful AI agent capable of analyzing patient
        journeys and deciding which point the patient is currently in and what the
        next steps are... */
        Load an AI Agent configuration document into memory
        /* Example:
        Documents:
        Patient Journey: https://documents/patientjopurney.txt
        APIs:
        Use this API when getting insurance information from Blue Cross Blue
        Shields of Colorado
        API URL: https://bcbs-colorado.com/apis/getpatientinfo
        JSON Payload:
            {
               "name": "getPatientInfo",
               "description": "Get patient info from the insurance number",
               "parameters": {
                 "type": "object",
                 "properties": {
                    "insuranceNumber": {
                       "type": "string",
                       "description": "Patient's insurance number."
                    }
                 }
                 "required": ["insuranceNumber"]
               }
            }
        */
        Concatenate the system prompt template and the AI Agent configuration
        file
        Set a system prompt for the LLM //This is to prime the AI model so it
        knows its context and what it can do, which tools (APIs) it is using
        Set a user prompt for the LLM to the task given by TCA
        Call the LLM API to generate a response
LLM:
        In the response to the API call, LLM returns a list of subtasks to the code
        module //Each sub-task has an indicator which tool (API) should be used
```

-continued

```
Code Module:
    Split the response into an array of strings //Each string array element is
    one subtask
    For each subtask in the array of subtasks
            Extract tool name from the subtask //e.g. WEB_SCRAPE_API
            Extract the subtask //e.g. https://insurance.com/apis?card=...
            Execute an API call with parameters
            Convert JSON to text
            Save the text in an array of responses
    EndFor
    Concatenate the responses and append an instruction to LLM to
    summarize information
    Set a user prompt for the LLM to the concatenated string from above
    Call the LLM API to generate a summary
    Return a summary to TCA
```

As evident from above, there is disclosed an example of intelligent automation achieved with multi-Agent AI cooperation which may results in minimum human efforts for checking in the patient at a place of care. For example, the hierarchy of chatbot application programs uses the set of data files 122 to describe the process and available data systems integrations so the process can be automated. Note that the set of data files is not required and there may be a single data file containing similar content based on which the hierarchy of chatbot application programs operates or behaves. Likewise, these technologies are applicable in medical care context, as disclosed herein, and other suitable contexts. For example, these technologies may be applicable in any field where there is an object (e.g., a physical object, a virtual object, a human, an animate object, an inanimate object, a tool, a device, a system, a container, a home, a vehicle) being serviced for which there is the process having the set of phases (e.g., creation, building, manufacturing, installation, maintenance, modification, uninstallation, removal, destruction) involving the object or information about or relating to the object, as disclosed herein.

Various embodiments of the present disclosure may be implemented in a data processing system suitable for storing and/or executing program code that includes at least one processor coupled directly or indirectly to memory elements through a system bus. The memory elements include, for instance, local memory employed during actual execution of the program code, bulk storage, and cache memory which provide temporary storage of at least some program code in order to reduce the number of times code must be retrieved from bulk storage during execution.

I/O devices (including, but not limited to, keyboards, displays, pointing devices, DASD, tape, CDs, DVDs, thumb drives and other memory media, etc.) can be coupled to the system either directly or through intervening I/O controllers. Network adapters may also be coupled to the system to enable the data processing system to become coupled to other data processing systems or remote printers or storage devices through intervening private or public networks. Modems, cable modems, and Ethernet cards are just a few of the available types of network adapters.

This disclosure may be embodied in a system, a method, and/or a computer program product. The computer program product may include a computer readable storage medium (or media) having computer readable program instructions thereon for causing a processor to carry out aspects of the present disclosure. The computer readable storage medium can be a tangible device that can retain and store instructions for use by an instruction execution device. The computer readable storage medium may be, for example, but not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present disclosure may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. A code segment or machine-executable instructions may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, among others. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In various embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer readable program instructions. The various illustrative logical blocks, modules, circuits, and algorithm steps described in connection with the embodiments disclosed herein may be implemented as electronic hardware, computer soft-ware, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

The flowchart and/or block diagrams in the figures illustrate the architecture, functionality, and operation of possible implementations of systems, methods, and computer program products according to various embodiments of the present disclosure. In this regard, each block in the flowchart and/or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Words such as "then," "next," etc. are not intended to limit the order of the steps; these words are simply used to guide the reader through the description of the methods. Although process flow diagrams may describe the operations as a sequential process, many of the operations can be performed in parallel or concurrently. In addition, the order of the operations may be re-arranged. A process may correspond to a method, a function, a procedure, a subroutine, a subprogram, etc. When a process corresponds to a function, its termination may correspond to a return of the function to the calling function or the main function.

Although various embodiments have been depicted and described in detail herein, skilled artisans know that various modifications, additions, substitutions and the like can be made without departing from this disclosure. As such, these modifications, additions, substitutions and the like are considered to be within this disclosure.

What is claimed is:

1. A system, comprising:
   a cloud computing instance, including a processor and a memory coupled to the processor, wherein the memory stores a set of instructions for execution by the processor, such that the processor is programmed to:
   access a data structure storing a first data file containing a listing of chatbot application programs recited in unstructured text, a second data file containing a set of configuration parameters recited in unstructured text, a third data file containing a set of prompt templates recited in unstructured text, a fourth data file containing a set of user types recited in unstructured text, and a fifth data file containing an outline of a process having a set of phases recited in unstructured text; and
   host a manager chatbot application program and a set of worker chatbot application programs, wherein the set of configuration parameters enables (i) the manager chatbot application program and the set of worker chatbot application programs to (ii) operate pursuant to the set of prompt templates custom to the set of user types (iii) based on the listing of chatbot application programs referencing the manager chatbot application program and the set of worker chatbot application programs, such that the manager chatbot application program:
      receives a prompt originating from a computing terminal, wherein the computing terminal is (i) external to the cloud computing instance and (ii) internal to a place of care having a staff member operating the computing terminal, wherein the prompt (i) requests a task be performed, (ii) identifies a patient associated with the place of care, and (iii) has been decorated based on at least one prompt template from the set of prompt templates according to at least one user type of the set of user types after the prompt is submitted into the computing terminal and before the manager chatbot application program receives the prompt;
      manages the set of worker chatbot application programs to perform a set of subtasks enabled to collectively perform the task pursuant to the set of phases as guided by the listing of chatbot application programs, the set of configuration parameters, the set of prompt templates, the set of user types, and the outline;
      generates a reply to the prompt based on the set of subtasks being performed by the set of worker chatbot application programs, thereby collectively performing the task; and
      sends the reply for consumption on the computing terminal responsive to the prompt.

2. The system of claim 1, wherein the data structure is a vector database.

3. The system of claim 1, wherein the manager chatbot application program has a one-to-many correspondence with the set of worker chatbot application programs.

4. The system of claim 1, wherein at least one worker chatbot application program of the set of worker chatbot application programs is programmed to access an application programming interface (API) external to the cloud computing instance, such that the API outputs a set of information to the at least one worker chatbot application program to enable the at least one worker chatbot application program to perform at least one subtask of the set of subtasks.

5. The system of claim 4, wherein the at least one worker chatbot application program accesses the API based on inputting a user identifier to the API, such that the set of information is specific to the user identifier and the at least one subtask is specific to the user identifier.

6. The system of claim 4, wherein the set of information is a speech-to-text transcription formed from a recording of an audio content.

7. The system of claim 6, wherein the prompt includes or references the recording.

8. The system of claim 6, wherein the at least one worker chatbot application program is programmed to form a summary of the speech-to-text transcription to enable the manager chatbot application program to take an action based on the summary.

9. The system of claim 8, wherein the at least one worker chatbot application program is a first worker chatbot application program, wherein the set of worker chatbot application programs contains a second worker chatbot application program, wherein the action is prompting the second worker chatbot application program.

10. The system of claim 1, wherein the cloud computing instance hosts a database storing a record containing a set of information for a user identifier, such that at least one worker chatbot application program of the set of worker chatbot application programs is programmed to perform at least one subtask of the set of subtasks relating to the user identifier by retrieving the set of information from the record, forming a summary of the set of information, and sending the summary to the manager chatbot application program to enable the manager chatbot application program to take an action based on the summary.

11. The system of claim 10, wherein the at least one worker chatbot application program is a first worker chatbot application program, wherein the at least one subtask is a first subtask, wherein the set of worker chatbot application programs contains a second worker chatbot application program, wherein the set of subtasks contains a second subtask, wherein the action is prompting the second worker chatbot application program to perform the second subtask relating to the user identifier.

12. The system of claim 1, wherein at least one worker chatbot application program of the set of worker chatbot application programs is programmed to access a first application programming interface (API) external to the cloud computing instance, such that the first API outputs a first set of information to the at least one worker chatbot application program to enable the at least one worker chatbot application program to perform at least one subtask of the set of subtasks, wherein the computing terminal is programmed to access a second API external to the cloud computing instance, such that the second API outputs a second set of information for consumption on the computing terminal, wherein the first API is logically positioned between the at least one worker chatbot application program and a data source, wherein the second API is logically positioned between the computing terminal and the data source.

13. The system of claim 12, wherein each of the first set of information and the second set of information relates to a user identifier, wherein the data source sources the first set of information or the second set of information based on the at least one worker chatbot application program or the computing terminal providing the first API or the second API with the user identifier, respectively.

14. The system of claim 13, wherein the first set of information and the second set of information is sourced from an electronic health record (EHR) associated with the user identifier.

15. The system of claim 1, wherein at least two worker chatbot application programs of the set of worker chatbot application programs are each programmed to access a first database and a second database, wherein the first database sources a first set of codes classified according to a first classification, wherein the second database sources a second set of codes classified according to a second classification.

16. The system of claim 1, wherein the set of subtasks includes a first subtask and a second subtask, wherein the first subtask involves an object detection algorithm or an edge detection algorithm performed on a medical image, such that a content is generated to enable the second subtask to be performed.

17. The system of claim 1, wherein the data structure is deployed external to the cloud computing instance.

18. The system of claim 1, wherein the set of subtasks corresponds to the set of phases.

19. The system of claim 18, wherein each worker chatbot application program of the set of worker chatbot application programs is programmed to be dedicated to performance of a single respective subtask of the set of subtasks.

20. The system of claim 1, wherein the data structure is deployed internal to the cloud computing instance.

21. The system of claim 1, wherein the set of worker chatbot application programs contains a first worker chatbot application program and a second worker chatbot application program, wherein the first worker chatbot application program is programmed to prompt the second worker chatbot application program.

22. The system of claim 1, wherein at least two subtasks of the set of subtasks is performed in sequence.

23. The system of claim 1, wherein at least two subtasks of the set of subtasks is performed out of sequence.

24. The system of claim 1, wherein at least two subtasks of the set of subtasks is performed in parallel.

25. The system of claim 1, wherein the manager chatbot application program is programmed to form the set of subtasks.

26. The system of claim 1, wherein at least one worker chatbot application program of the set of worker chatbot application programs is programmed to form the set of subtasks.

* * * * *